United States Patent
Atkinson et al.

(10) Patent No.: US 6,878,949 B2
(45) Date of Patent: Apr. 12, 2005

(54) GEL IMAGING AND EXCISION

(75) Inventors: George Robert Atkinson, Dorset (GB); Robert Woodrough, Dorset (GB)

(73) Assignee: Genextix Limited, Hampshire (GB)

( * ) Notice: Subject to any disclaimer, the term of this patent is extended or adjusted under 35 U.S.C. 154(b) by 187 days.

(21) Appl. No.: 10/225,302

(22) Filed: Aug. 22, 2002

(65) Prior Publication Data

US 2004/0036036 A1 Feb. 26, 2004

(51) Int. Cl.$^7$ ............................................. G01N 21/64
(52) U.S. Cl. ............................... 250/461.2; 250/458.1; 422/82.08
(58) Field of Search ...................... 250/461.2, 461.1, 250/459.1, 458.1; 422/82.08

(56) References Cited

U.S. PATENT DOCUMENTS

| | | | |
|---|---|---|---|
| 4,824,547 A | * 4/1989 | Zhang et al. | ............... 204/462 |
| 5,307,148 A | 4/1994 | Kambara et al. | |
| 5,534,386 A | * 7/1996 | Petersen et al. | ............ 430/320 |
| 5,587,062 A | 12/1996 | Togawa et al. | |
| 5,774,214 A | * 6/1998 | Prettyjohns | ................ 356/344 |
| 6,071,748 A | * 6/2000 | Modlin et al. | .............. 436/174 |
| 6,198,107 B1 | 3/2001 | Seville | |
| 6,403,970 B1 | * 6/2002 | Hung | ...................... 250/458.1 |
| 6,512,236 B2 | * 1/2003 | Seville | .................... 250/458.1 |
| 2002/0108857 A1 | * 8/2002 | Paschetto et al. | ........... 204/457 |
| 2003/0155528 A1 | * 8/2003 | Tokuda | .................... 250/461.2 |
| 2003/0160182 A1 | * 8/2003 | Petrich et al. | ........... 250/458.1 |
| 2003/0189178 A1 | * 10/2003 | Wagoner et al. | ......... 250/459.1 |
| 2003/0230728 A1 | * 12/2003 | Dai et al. | ............... 250/458.1 |

FOREIGN PATENT DOCUMENTS

| | | |
|---|---|---|
| EP | 0 840 114 A2 | 5/1998 |
| EP | 1 160 564 A2 | 12/2001 |
| JP | 7-260742 | 10/1995 |
| WO | WO 98/23950 A1 | 6/1998 |
| WO | WO 99/51977 A1 | 10/1999 |

* cited by examiner

Primary Examiner—Albert Gagliardi
(74) Attorney, Agent, or Firm—Foley & Lardner LLP

(57) ABSTRACT

A robot for imaging and excision of two-dimensional fluorescent gels. An array detector is mounted in the roof of the robot to image down onto a gel dish placed on a light table. Fluorescence is excited by illuminating the light table from below with light emitting diodes mounted under the main bed of the apparatus. It is therefore possible to perform gel fluorescence analysis and coring (excision) using the same machine. The integration is based on a transmission mode optical design, distinct from prior art scanners and imagers which are based on reflection mode designs. This approach allows the conventional layout of a microarraying or picking robot to be maintained, avoiding unnecessary redesign of other robot functions associated with well plate and container handling. The apparatus may also be used for contrast imaging of non-fluorescent gels.

14 Claims, 6 Drawing Sheets

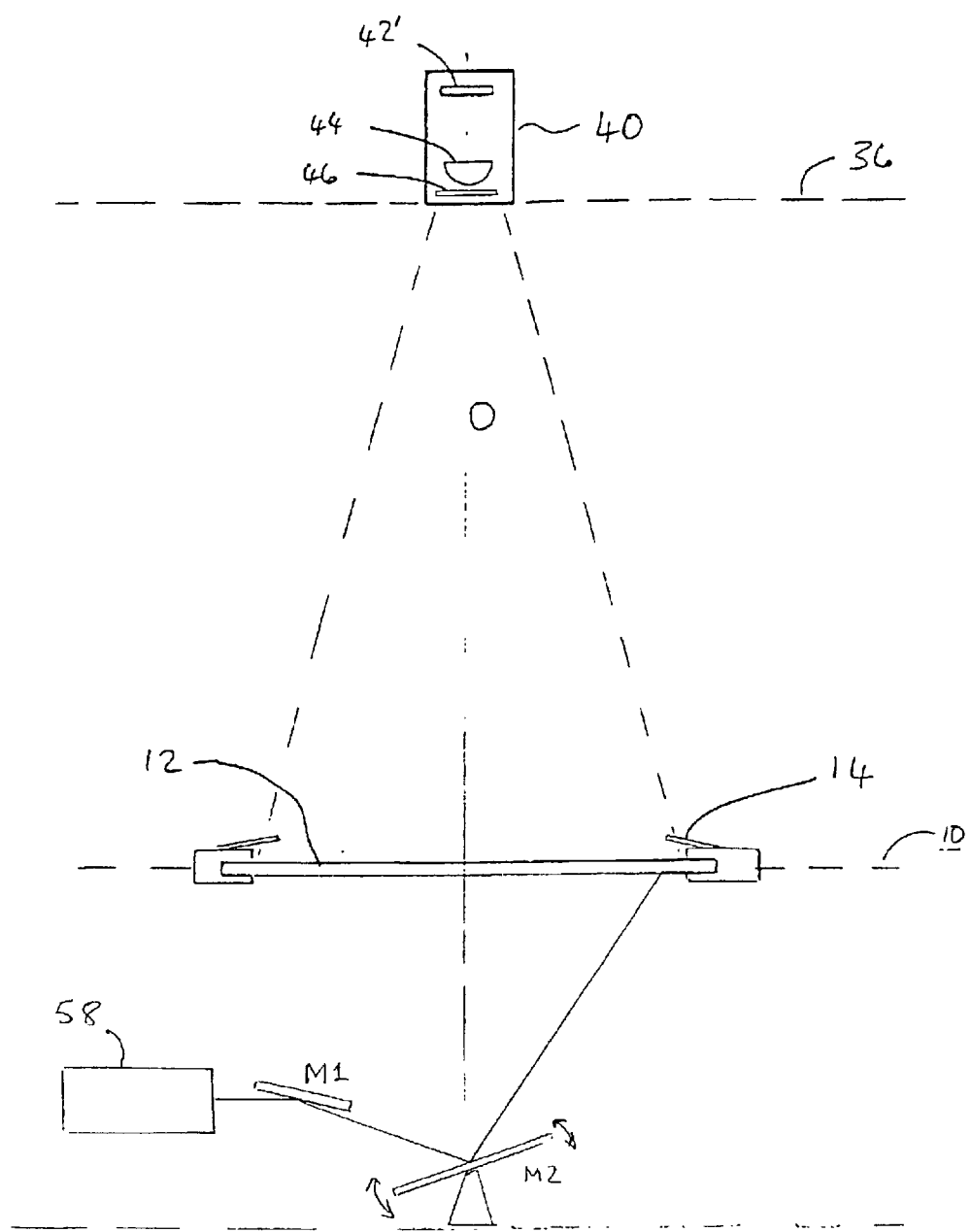

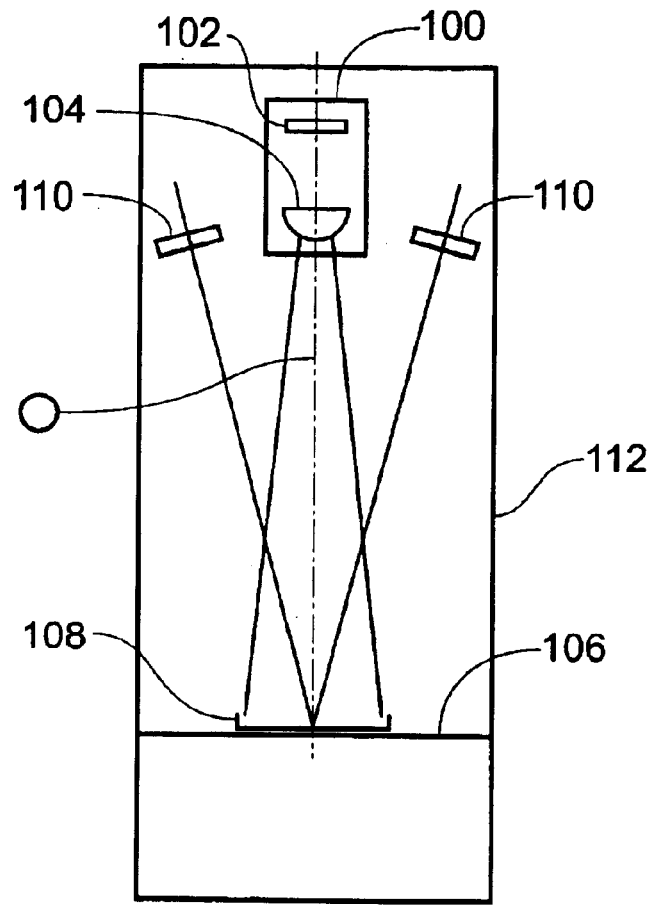
Fig. 6 -- Prior Art--
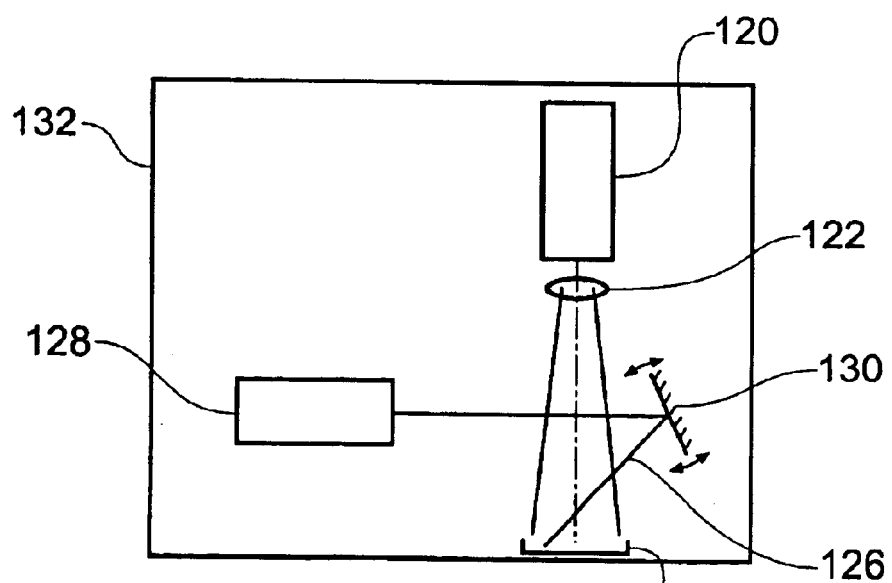
Fig. 7 --Prior Art--

GEL IMAGING AND EXCISION

BACKGROUND OF THE INVENTION

The invention relates to imaging of gels stained with fluorescent material, in particular to imaging of two-dimensional gels such as protein gels, but also to imaging of one-dimensional gels, such as electrophoresis gels. The invention further relates to excision of gel material on the basis of its fluorescence.

Protein gels are used in various biochemical processes. Proteins are manipulated in one or two dimensions in a gel. For example, manipulation may be in the form of protein migration, where migration rate depends on protein molecule size with the smallest proteins moving fastest. Another kind of manipulation is based on response to an electric field which can be used to force alkali and basic proteins to move in opposite directions with a migration rate that depends on the degree of alkalinity or acidity. So-called two-dimensional gels allow protein migration based on size and acidity to be performed in orthogonal directions in the same gel.

To measure the locations of the proteins in the gel, the proteins are marked with a fluorescent stain. The fluorescence is then measured in an optical device which includes an excitation source and photodetection device. The amount of protein at a particular location is inferred from the strength of the fluorescence measured at that point by the photodetection device.

Once a gel location of interest has been located by the optical device, by virtue of its strong fluorescence, that part of the gel is typically removed and placed in the well of a well plate for further processing. This is done conventionally by transferring the gel dish to a robot fitted with a gel coring head. The gel coring head is fitted with a number of corers, for example 8, which can cut out and suck up circular cross-section plugs of gel and deposit them into a well of a well plate.

A large number of fluorescent stains are known. The stains typically have relatively broadband characteristics with one or more broad absorption or excitation bands and a single strong broad emission band. A widely used fluorescent stain is sypro ruby which has excitation bands in the ultraviolet (UV) and blue and emits in the red, peaked at around 620 nm.

Two kinds of optical device are known for measuring gel fluorescence, as now described with reference to the figures.

FIG. 6 is a schematic side view of an imager in which a charged coupled device (CCD) detector unit 100 comprising a CCD chip 102 and objective 104 is arranged above a shelf 106 on which a gel dish 108 can be placed centrally about the optical axis "O" of the CCD detector unit 100. Alongside the CCD detector unit 100, banks of blue light emitting diodes (LEDs) 110 are arranged facing the center of the shelf where gel dishes are to be placed. The blue LED banks 110 are used to excite fluorescence in the gel which is then measured by the CCD chip. The imager is built into a light-tight housing 112 accessed by a hinged door (not shown). An imager of this kind is the Fuji LAS-1000.

FIG. 7 is a schematic side view of a scanner in which a photomultiplier tube (PMT) 120 and objective 122 are used to measure fluorescence from a gel contained in a gel dish 124 which is excited by raster scanning a 488 nm laser beam 126 generated by an argon ion laser 128 over the gel dish. Raster scanning is achieved by a movable mirror arrangement 130. The scanner is arranged in a light tight housing 132.

It will thus be appreciated that the principal difference between the imager and the scanner is that the imager is a parallel device and the scanner a serial device.

The imager is quicker, but suffers from the limitation that the blanket illumination from the LEDs provides a non-uniform intensity distribution across the gel, which results in errors in the correlation between protein density and fluorescence intensity. This problem is exacerbated by the CCD chip imaging the reflections of individual LEDs themselves as well as the gel.

The scanner provides uniform illumination, since the argon ion laser can be well power stabilized, but is slow. Moreover, use of an argon laser is undesirable since it is a bulky inefficient item that may need air or water cooling and three-phase power supply depending on the optical power required.

As is also apparent, both the scanner and the imager are stand-alone devices. Excision of the gel material identified by the fluorescence analysis needs to be performed in a separate machine, namely a robot with excision capability.

SUMMARY OF THE INVENTION

According to one aspect of the invention there is provided a robotic apparatus comprising: a main bed fitted with a light table plate on which a gel dish can be placed; a head with associated positioning system mounted above the main bed of the apparatus; an array detector mounted to image the light table plate from above; and a plurality of light emitting diodes mounted under the main bed of the apparatus to illuminate the light table plate from below.

The invention can thus provide an excision robot integrated with a transmission mode optical system in which the fluorescence excitation optics are mounted under the main bed of the robot illuminating a conventional light table surface from underneath and a photodetection device is mounted above the light table in the lid of the excision robot staring down onto the light table. It is therefore possible to perform gel fluorescence analysis and coring using the same machine. The integration is based on a transmission mode optical solution, distinct from prior art scanners and imagers which are based on a reflection mode optical design.

The adopted transmission mode solution is based around a conventional light table platform that is a standard option for picking robots. Consequently, no redesign of ancillary robotic functions is necessary. In particular, the light-table-based solution leaves the whole of the above-bed area free for other tasks. Specifically, conventional xyz-positioners can be used to move a gel coring head (or other head) freely around the robot without any additional motion constraints to perform excision. Moreover, the whole bed area of the robot is still available for conventional uses, such as placement of well plates, Q-trays etc; liquid handling, provision of shakers, delidders, waste chutes, cleaning baths and so forth.

Additionally it has been realized that blanket illumination with light emitting diodes is greatly enhanced by allowing the light emitted by the light emitting diodes to interact with a diffuser, preferably a holographic diffuser, before illuminating the gel. Preferably, the diffuser is transmissive and placed in front of the light emitting diodes.

The apparatus thus preferably further comprises a diffuser arranged between the light emitting diodes and the light table plate in order to equalize the intensity distribution of light from the light emitting diodes that is incident on the light table plate.

Provision of a uniform intensity distribution across the gel is important for fluorescence imaging, since fluorescence intensity is proportional to excitation intensity, so that spatial variance in the imaging intensity is a source of error. This is because the analysis has to assume that there is a direct correlation between protein density and fluorescence intensity. Uniform illumination is also important for contrast imaging for which the apparatus can also be used.

Appropriate filtering should be used when the apparatus is intended for fluorescence imaging. (In embodiments of the invention that are based on contrast imaging, filtering may not be needed.) In the preferred embodiment for fluorescence imaging a detection-side filter is arranged between the light table plate and the array detector and has a response that passes wavelengths lying in an emission band of a fluorescent stain to be used and blocks wavelengths lying in an excitation band of the fluorescent stain. Moreover, an excitation-side filter is arranged between the light emitting diodes and the light table plate and has a response that blocks wavelengths lying in the emission band of the fluorescent stain. This increases the image contrast between the fluorescent stain and the background.

The light emitting diodes are selected to output light at wavelengths lying in an excitation band of a fluorescent stain to be used. For example, 473 nm blue light emitting diodes are suitable for exciting fluorescence in sypro ruby.

The apparatus can be made more versatile by providing light emitting diodes of different types, for example a first group for outputting in a first wavelength band (e.g. blue) and a second group for outputting in a second wavelength band (e.g. green, red). The apparatus can then be used with different fluorescent and non-fluorescent stains by operating the group of light emitting diodes of the appropriate type. As further light emitting diode types become commercially available (e.g. in the ultraviolet), more groups can be provided so that the apparatus can be developed to become more versatile.

It will be appreciated that the apparatus can be fitted with a gel coring head. The gel corers can be used in conjunction with the imaging system to remove gel samples of interest from a gel dish and place them in a well plate that will also be arranged on the main bed of the apparatus. Fully integrated image processing and gel sample preparation can thus be provided. An important practical advantage here is that the imaging system used to identify the gel samples of interest in the gel dish (by fluorescence or contrast imaging) is the same imaging system as used by the robotic apparatus to guide the gel corer to the correct coordinates for sample removal. This eliminates a major source of image processing difficulty and error when using a stand-alone imager and the machine vision system of a standard robot (typically a CCD camera mounted on the head) which will usually be quite different so that it may not be trivial to reliably link a coordinate measured in the imager to a coordinate on the robot.

The light table plate is preferably made of translucent acrylic or glass material, such as opal acrylic or shot-blasted glass.

The array detector is preferably a charged coupled device (CCD). Alternatively other two-dimensional array detectors, such as multi-channel plates (MCPs), could be used. The array detector may be cooled, for example with a Peltier device or using a cryogen such as liquid nitrogen. A one-dimensional array detector could also be used, such as a line-scan camera. This would be suitable for use in conjunction with 1D gels, for example.

As already mentioned, use of a diffuser has been found to greatly improve the uniformity of illumination intensity from light emitting diodes. Comparative tests have shown that light emitting diode illumination through a diffuser is in fact superior to white light illumination from conventional strip lights even for contrast imaging (i.e. even when the gel is stained with a non-fluorescent stain such as silver stain). It is therefore proposed to use light emitting diode illumination through a diffuser not only for fluorescence imaging, but also for contrast imaging.

Accordingly, a second aspect of the invention provides an imager comprising: a sample area where a gel dish can be placed; an array detector mounted to image the sample area; a plurality of light emitting diodes mounted to illuminate the sample area; and a diffuser arranged between the light emitting diodes and the sample area in order to equalize the intensity distribution of light from the light emitting diodes that is incident on the sample area.

The light emitting diodes may be mounted to illuminate the sample area from the same side as the side from which the array detector images the sample area to provide a reflection mode imager similar to the prior art but with the enhancement of a diffuser, preferably a holographic diffuser. Alternatively, the light emitting diodes may be mounted to illuminate the sample area from the opposite side from the side from which the array detector images the sample area to provide a transmission mode imager optically similar to the proposed robotic excision apparatus.

Alternatively, the apparatus of the first aspect of the invention based on transmission mode optics could be modified by using a laser source, such as an ion laser, in place of the light emitting diodes and scanning the laser beam over the light plate's lower surface. In this case a single channel detector could be used. Suitable ion lasers include argon ion and krypton ion sources.

Accordingly, a third aspect of the invention provides a robotic apparatus comprising: a main bed fitted with a light table plate on which a gel dish can be placed; a head with associated positioning system mounted above the main bed of the apparatus; a detector mounted to view the light table plate from above; and a laser mounted under the main bed of the apparatus to scan a laser beam over the light table plate from below. It will be appreciated that the beam scanning can be performed with appropriate scanning mirror optics.

BRIEF DESCRIPTION OF THE DRAWINGS

For a better understanding of the invention and to show how the same may be carried into effect reference is now made by way of example to the accompanying drawing which show:

FIG. 5 is a schematic side view showing the optical design of an alternative apparatus embodying the invention;

FIG. 6 shows the principles of a prior art imager; and

FIG. 7 shows the principles of a prior art scanner.

DETAILED DESCRIPTION

Figure 1:
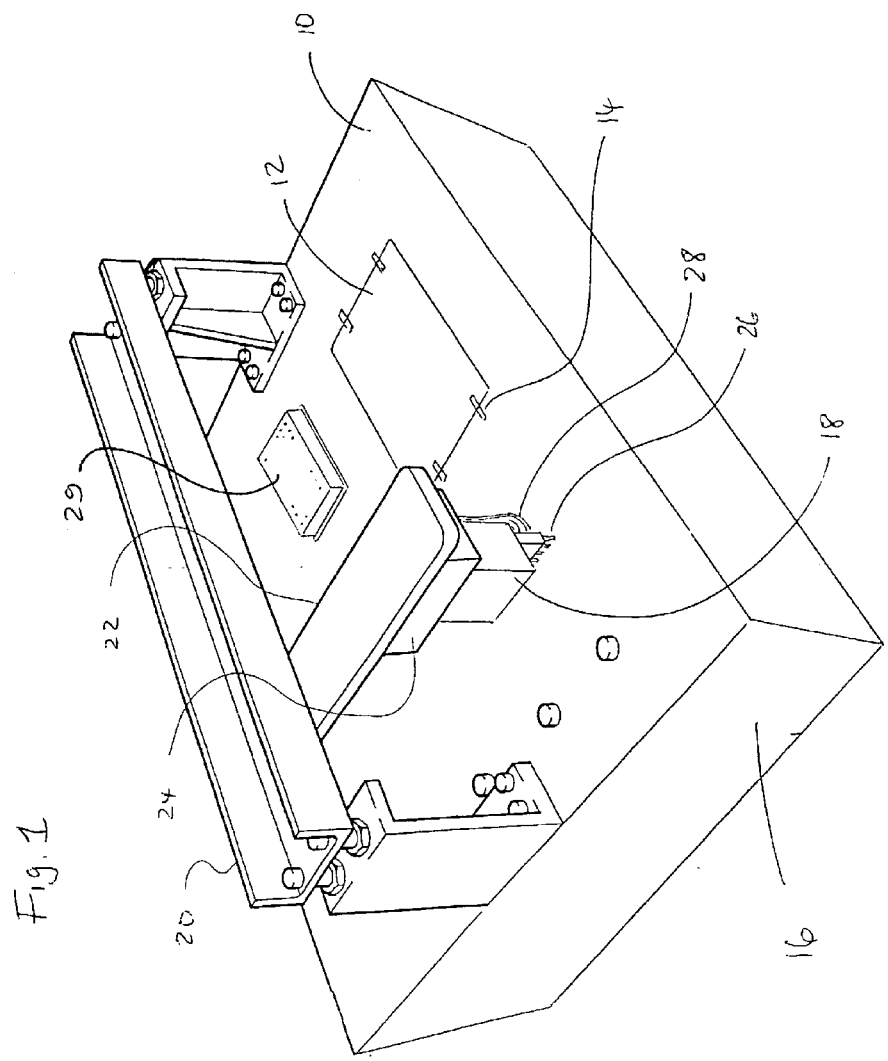
FIG. 1 is a perspective view of the lower part of an apparatus embodying the invention.

FIG. 1 is a perspective view of the lower part of an apparatus embodying the invention. The upper part is not shown in order to reveal the main bed 10 of the apparatus. A light table plate 12 made of a translucent material, known as opal acrylic, is mounted flush with the main bed. A set of clamps 14 (four in the figure) is provided around the periphery of the light table plate 12 for locating and securing gel dishes, such as Q-trays, on the light table. The light table plate is illuminated from below by optical equipment accommodated under the main bed in the space provided in the apparatus's main base 16.

The apparatus has a manipulation head 18, a gel coring head in the figure, which is movable over the main bed of the apparatus by x- y- and z-positioners 20, 22 and 24 respectively. The gel coring head illustrated comprises an array of gel corers 26, each gel corer having the form of a hollow pin connected to an air feed line. In one example, the head has a 1×8 array of corers with each gel corer 26 having its own air feed line 28 for suction and expulsion of a plug of gel material to perform excision from a gel dish followed by deposition of the excised gel sample plug into a well of a well plate or other target location. The manipulation head 18 is carried by the z-positioner, which is in turn carried by the y-positioner, which is carried by the x-positioner. Adjacent the manipulation head 18 the z-positioner may also have attached thereto a well plate gripper (not shown) to allow well plates to be moved around the main bed of the apparatus. The manipulation head 18 is detachably mounted on the z-positioner so that the head type can be changed. A gel coring head would be fitted for excision. Other heads may be needed for gel-based processes. For example, gel-based processes of this kind may involve liquid handling to and from well plates in which a liquid handling head having an array of micropipette tips would be fitted. Head exchange is assumed to be manually performed in the illustration, but automated head exchange could be provided.

A single well plate 29 is illustrated on the main bed of the apparatus by way of example. The main bed may be provided with stations for well plates and gel dishes of various standard types. The main bed may also include other standard equipment such as a waste chute, a well plate delidder, well plate shakers, well plate hotel, and a wash station. None of these is illustrated. The apparatus may also be provided with an automated well plate feeding and stacking mechanism and an automated gel dish feeding and stacking mechanism. Neither is shown.

Figure 2:
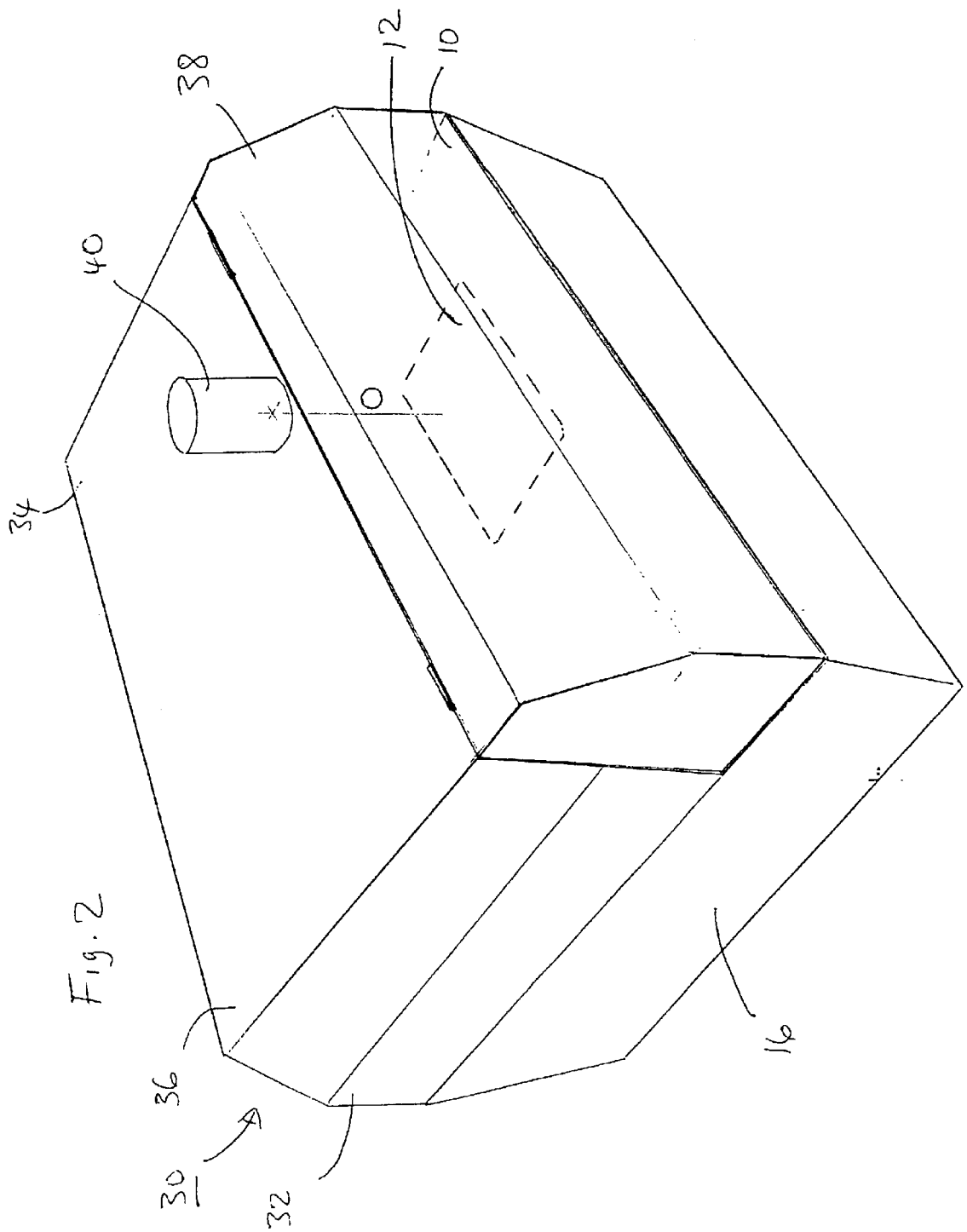
FIG. 2 is a perspective view of the apparatus embodying the invention.

FIG. 2 is a perspective view of the apparatus embodying the invention. In comparison to FIG. 1, the apparatus also shows the upper part of the machine. The upper part is principally formed of a light-tight cover 30 with two sides 32, a back 34 and a roof 36. On the front side of the machine there is a hinged door 38 to provide access. Mounted in the roof, there is a detector unit 40 housing an array detector, in the form of a CCD chip, and associated imaging optics, in the form of an objective lens and an appropriate filter. The imaging optics are designed to have the upper surface of the light table plate as the imaging plane, or a slightly higher plane to take account of the usual thickness of the gel dish base. The CCD chip is cooled with a Peltier cooler (not shown). If a lower operating temperature is desired to further reduce noise, a cryogen such as liquid nitrogen could be used, for example with a closed cycle cryostat. The detector unit 40 is contained in a cylindrical housing bolted upright on the roof of the machine so that the principal optical axis "O" of the detector unit is perpendicular to the plane of the main bed of the apparatus. Optical access to the light table below is provided by an aperture in the roof.

Figure 3:
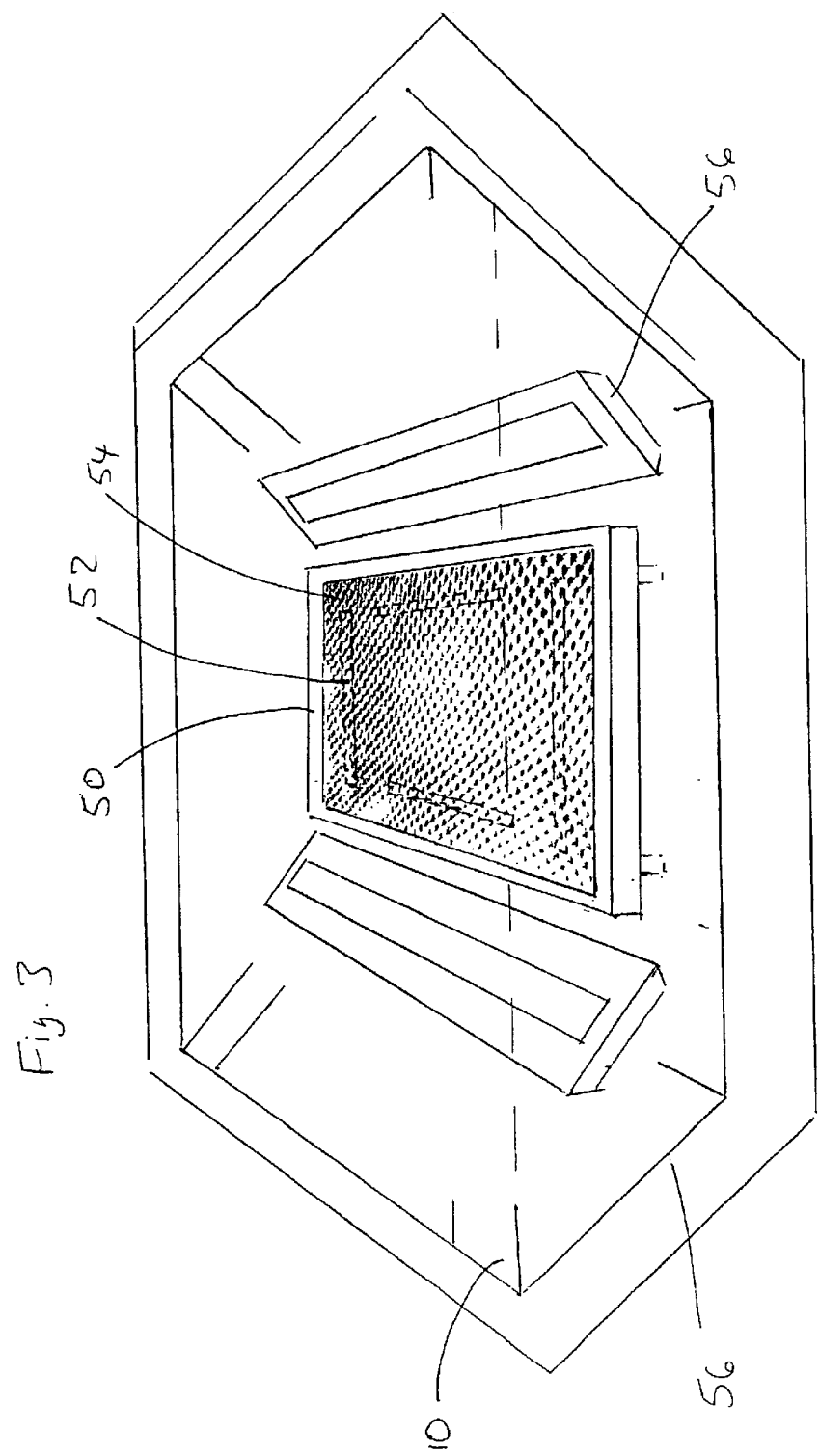
FIG. 3 shows features of the light table illumination system of the apparatus embodying the invention.

FIG. 3 shows features of the light table illumination system of the apparatus embodying the invention. The figure is a perspective view from one side of the machine from a position looking down onto and across the plane of the main bed of the machine, but with the main bed not shown. The plane of the main bed (and the light table plate) is marked with reference numeral 10. The main part of the illumination system is a source unit 50 which is rectangular in footprint having dimensions approximately matching those of the light table illumination plate (e.g. about 300×200 mm) and which has a thickness of approximately 20 mm. Arranged in the base of the source unit is a plurality of blue light emitting diodes (LEDs) that emit at a nominal center wavelength of 473 nm. (In other embodiments different color LEDs could be used.) The LEDs are arranged in four banks 52 (dashed lines) with each bank being a packaged unit of 100 surface mounted LEDs with an integrated Fresnel lens. Alternatively, discrete LEDs could be used spread over the area of the source unit. Arranged over the LEDs covering the whole area of the source unit is a sheet of filter (not shown) followed by a sheet of holographic diffuser 54. The holographic diffuser is a sheet of plastic material with a microsculpted surface relief structure made by an embossing process using a holographically produced blank (see e.g. U.S. Pat. No. 5,534,386: Physical Optics Corporation [1]). The diffuser homogenizes the LED light output, so that the intensity distribution of light from the LEDs on the light table plate is equalized. Arranged on either side of the source unit there are strip light units 56 for providing white light illumination to the light table plate for contrast imaging.

Figure 4:
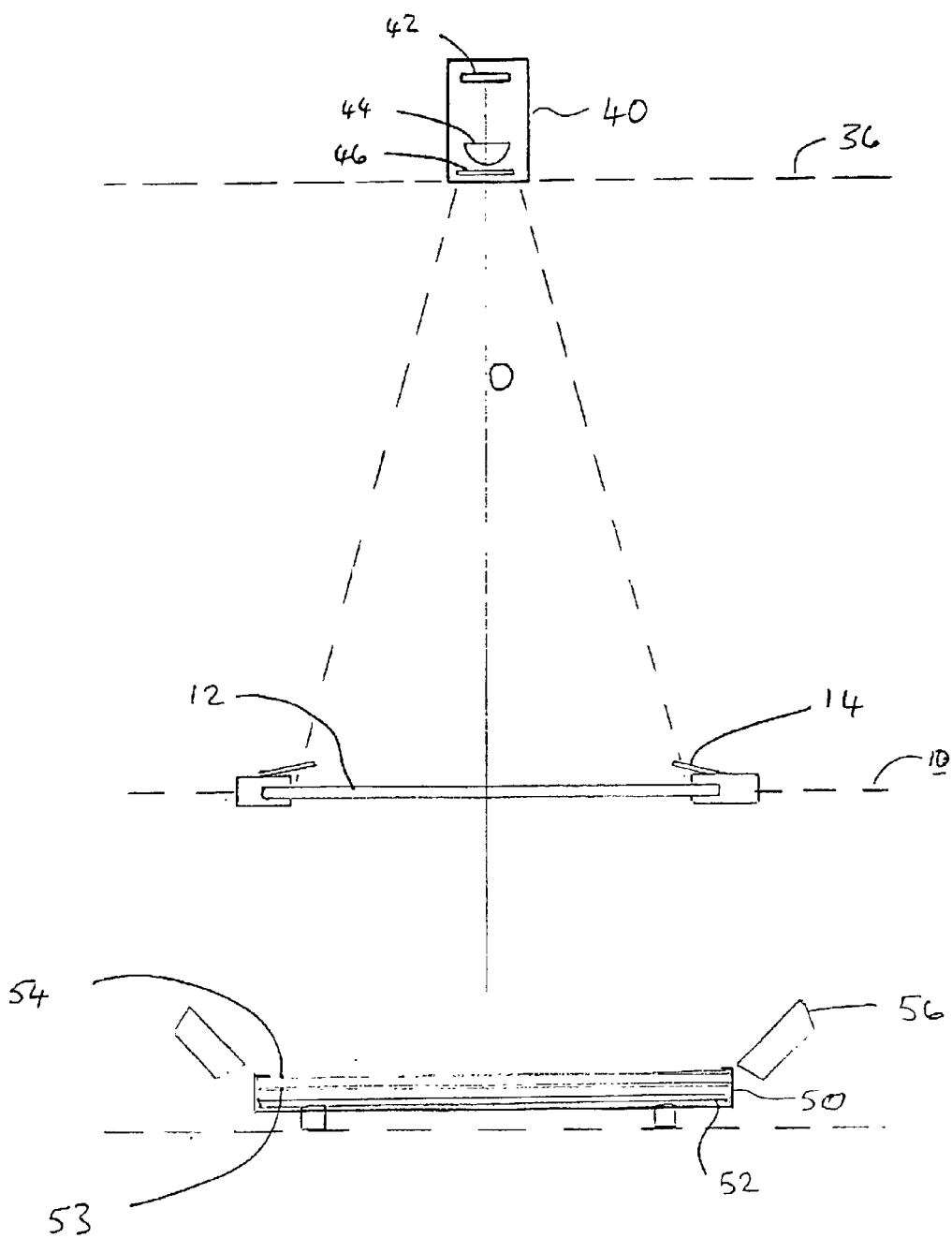
FIG. 4 is a schematic side view showing the optical design of the apparatus embodying the invention.

FIG. 4 is a schematic side view showing the optical design. At the top of the figure, the detector unit 40 can be seen mounted on the roof 36. The detector unit 40 contains a CCD chip 42 with associated collection optics 44 illustrated schematically as a single objective lens. It will be appreciated that any appropriate lens (or mirror) combination may be used in order to image the light table area onto the active surface of the CCD chip. The optical axis "O" of the detector unit 40 is also shown. The detector unit 40 also includes a filter 46. This is a bandpass filter for filtering out the LED output. A 620 nm with 35 nm bandpass is selected for the blue LEDs mentioned above. It will be appreciated that in general an appropriate selection of bandpass or cutoff filter will be made having regard to the output response of the LEDs, and the excitation and emission bands of the fluorescent stain to be used. Moreover, in some applications, for example with contrast imaging, a filter may be dispensed with. In the middle of the figure, the light table plate 12 and gel dish clamps 14 are illustrated, with the light table plate 12 lying generally in the plane of the apparatus main bed 10. At the bottom of the figure, the light source unit 50 is shown with its LEDs 52, filter 53 and diffuser 54. The filter 53 is a bulk dyed band pass filter of the kind used for theatrical lighting which is blue in the present example where blue LEDs are used. The filter 53 is effective for removing undesired components of the LED output. Specifically in the case of blue LEDs it has been found that a small proportion of the LEDs malfunction by emitting wavelength components outside the blue into the green and red. A different color filter can be chosen depending on the output wavelengths of the LEDs used. The angled strip light units 56 are also evident.

In practice, it has been found that a CCD exposure time of around 1–3 minutes is sufficient to image gels stained with sypro ruby using the blue LED based implementation described above. The exposure time is proportional to illumination intensity, so that exposure time can be reduced by using more LEDs and more powerful LEDs. As blue LEDs in particular become more powerful and less costly it is expected that exposure times can be reduced considerably.

FIG. 5 is a schematic side view showing the optical design of an alternative embodiment. The light table and detector parts are generally the same as in the optical design of FIG. 4, although the detector 42' is a single channel detector such as a photomultiplier tube rather than a CCD chip. The optical design differs from that of the embodiment of FIG. 4 in that an ion laser 58 is used as the light source in order to generate a laser beam that is raster scanned (or line scanned) over the underside of the light table plate 12 by directing it with a static mirror M1 and a deflectably mounted scanning mirror M2. As in the embodiment of FIG. 4, the light source is conveniently mounted in the space under the main bed of the apparatus. The embodiment of FIG. 5 is thus similar to that of FIG. 4 in that it is based on transmission mode optics with the optical source equipment mounted under the main bed of the apparatus, but differs from the embodiment of FIG. 4 in that it is based on serial excitation and detection instead of parallel excitation and detection. It will be understood that other laser sources could be used in place of an ion laser, for example a He—Cd laser.

The invention has been described in terms of staining gels. It will be understood that the apparatus is applicable to any material that can be stained with fluorescent or non-fluorescent stains.

Moreover, the invention has been described principally in terms of the fluorescent stain sypro ruby. Other fluorescent stains are available emitting across the visible from ultraviolet, to blue, green, orange and red. It will be understood that the proposed design can be readily modified to use with any desired fluorescent stain with suitable adaptation of the optical sources, filters and detector. Specifically, the invention can be applied to cy3 and cy5 stains available from Amersham Biosciences. Non-fluorescent stains to which the invention can be applied are silver stain and coomassie blue stain (sometimes referred to as brilliant blue stain). For contrast imaging of non-fluorescent stains, such as coomassie blue, tests have shown that an orange excitation filter can produce a significant improvement in image contrast. Alternatively red LEDs may be suitable.

It will also be understood that although the term light emitting diode is used commonly in the art to describe only one type of light source based on diode emission, the term light emitting diodes is to be construed broadly in the claims of the present document to cover all forms of light emitting diode sources, including diode lasers, such as semiconductor diode lasers, and superluminescent diodes.

REFERENCES

[1] U.S. Pat. No. 5,534,386: Physical Optics Corporation

What is claimed is:

1. A robotic apparatus comprising:
a main bed fitted with a light table plate on which a gel dish can be placed;
a head with associated positioning system mounted above the main bed of the apparatus;
an array detector mounted to image the light table plate from above; and
a plurality of light emitting diodes mounted under the main bed of the apparatus to illuminate the light table plate from below.

2. The apparatus of claim 1, further comprising a diffuser arranged between the light emitting diodes and the light table plate in order to equalize the intensity distribution of light from the light emitting diodes that is incident on the light table plate.

3. The apparatus of claim 2, wherein the diffuser is a holographic diffuser.

4. The apparatus of claim 1, wherein a detection-side filter is arranged between the light table plate and the array detector and has a response that passes wavelengths lying in a fluorescence band of a fluorescent stain to be used.

5. The apparatus of claim 1, wherein an illumination-side filter is arranged between the light emitting diodes and the light table plate and has a response that blocks wavelengths lying in a fluorescence band of a fluorescent stain to be used and passes wavelengths lying in an excitation band of the fluorescent stain.

6. The apparatus of claim 1, wherein a detection-side filter is arranged between the light table plate and the array detector and has a response that passes wavelengths lying in an emission band of a fluorescent stain to be used and blocks wavelengths lying in an excitation band of the fluorescent stain, and wherein an excitation-side filter is arranged between the light emitting diodes and the light table plate and has a response that blocks wavelengths lying in the emission band of the fluorescent stain.

7. The apparatus of claim 1, wherein the light emitting diodes output light at wavelengths lying in an excitation band of a fluorescent stain to be used.

8. The apparatus of claim 1, wherein the light emitting diodes are blue light emitting diodes.

9. The apparatus of claim 1, wherein the light emitting diodes include a first group for outputting in a first wavelength band and a second group for outputting in a second wavelength band.

10. The apparatus of claim 1, wherein the head comprises a plurality of gel corers.

11. The apparatus of claim 1, wherein the light table plate is made of translucent acrylic or glass material.

12. The apparatus of claim 1, wherein the array detector is a charged coupled device (CCD).

13. The apparatus of claim 12, wherein the CCD is provided with a cooling device.

14. A robotic apparatus comprising:
a main bed fitted with a light table plate on which a gel dish can be placed;
a head with associated positioning system mounted above the main bed of the apparatus;
a detector mounted to view the light table plate from above; and
a laser mounted under the main bed of the apparatus to scan a laser beam over the light table plate from below.

* * * * *

UNITED STATES PATENT AND TRADEMARK OFFICE
CERTIFICATE OF CORRECTION

PATENT NO. : 6,878,949 B2 Page 1 of 1
DATED : April 12, 2005
INVENTOR(S) : George Robert Atkinson et al.

It is certified that error appears in the above-identified patent and that said Letters Patent is hereby corrected as shown below:

Title page,
Item [73], Assignee, change "Genextix Limited" to -- Genetix Limited --.

Signed and Sealed this

Seventh Day of February, 2006

JON W. DUDAS
*Director of the United States Patent and Trademark Office*